United States Patent
Egana-Erazo

(10) Patent No.: US 11,452,740 B2
(45) Date of Patent: Sep. 27, 2022

(54) PHOTOSYNTHETIC CELLULAR SUBSTANCES AND METHODS OF USE THEREOF

(71) Applicant: SYMBIOX, INC., San Diego, CA (US)

(72) Inventor: Jose-Tomas Egana-Erazo, Santiago (CL)

(73) Assignee: SYMBIOX, INC.

( * ) Notice: Subject to any disclaimer, the term of this patent is extended or adjusted under 35 U.S.C. 154(b) by 0 days.

(21) Appl. No.: 14/845,063

(22) Filed: Sep. 3, 2015

(65) Prior Publication Data

US 2016/0058861 A1    Mar. 3, 2016

Related U.S. Application Data

(60) Provisional application No. 62/092,229, filed on Dec. 15, 2014, provisional application No. 62/045,523, (Continued)

(51) Int. Cl.
*A61N 5/06* (2006.01)
*A61K 33/00* (2006.01)

(52) U.S. Cl.
CPC ............ *A61K 33/00* (2013.01); *A61N 5/0616* (2013.01); *A61N 2005/0651* (2013.01)

(58) Field of Classification Search
CPC ...... A61N 5/06; A61N 5/0613; A61N 5/0616; A61N 5/062; A61N 5/0624;
(Continued)

(56) References Cited

U.S. PATENT DOCUMENTS 5,330,741 A * 7/1994 Smith .................. C07D 487/22
                                                   424/9.61
5,792,090 A    8/1998 Ladin
(Continued)

FOREIGN PATENT DOCUMENTS

| WO | 2008070741 A1 | 6/2008 |
| WO | 2014058532 A1 | 4/2014 |

OTHER PUBLICATIONS

Mehrabani et al., "Preparation of biocompatible and biodegradable silk fibroin/chitin/silver nanoparticles 3D scaffolds as a bandage for antimicrobial wound dressing," International Journal of Biological Macromolecues 114 (2018) 961-971.*

(Continued)

*Primary Examiner* — Ahmed M Farah
(74) *Attorney, Agent, or Firm* — Procopio, Cory, Hargreaves & Savitch LLP

(57) ABSTRACT

Systems and methods for developing and applying photosynthetic cellular substances to a human or animal for medical, therapeutic or cosmetic uses are provided. Photosynthetic cells, such as algal cells, can be used in these substances to provide the ability to continuously generate oxygen when exposed to a light source or other oxygen-generating trigger. The substances can be developed as a standalone liquid, gel or cream, or embedded within a bandage, mesh, scaffold or other structure with a light source to promote oxygen production. The substances can be applied topically for medical, therapeutic or cosmetic treatments, or injected internally for generation of oxygen within one or more parts of the body.

11 Claims, 6 Drawing Sheets

Related U.S. Application Data filed on Sep. 3, 2014, provisional application No. 62/045,527, filed on Sep. 3, 2014, provisional application No. 62/045,524, filed on Sep. 3, 2014, provisional application No. 62/045,530, filed on Sep. 3, 2014, provisional application No. 62/045,525, filed on Sep. 3, 2014, provisional application No. 62/045,528, filed on Sep. 3, 2014.

(58) Field of Classification Search
CPC .... A61N 2005/0632; A61N 2005/0635; A61N 2005/0645; A61N 2005/065; A61N 2005/0651; A61N 2005/0652; A61N 2005/0653; A61N 2005/0658; A61N 2005/0661; A61N 2005/0662; A61N 2005/0663; A61K 36/00; A61K 36/02; A61K 36/03; A61K 36/04; A61K 36/05; A61K 36/06; A61K 36/09; A61K 36/10; A61K 36/11; A61K 36/18
USPC .......................... 606/88–92; 609/9; 128/898
See application file for complete search history.

(56) References Cited

U.S. PATENT DOCUMENTS

| | | | |
|---|---|---|---|
| 6,443,978 B1* | 9/2002 | Zharov | A61N 5/0616 607/91 |
| 7,753,894 B2* | 7/2010 | Blott | A61M 1/0037 128/897 |
| 7,794,450 B2* | 9/2010 | Blott | A61M 35/00 604/543 |
| 8,372,128 B2* | 2/2013 | Reuben | A61F 13/0203 607/88 |
| 8,679,523 B2 | 3/2014 | Gibbins et al. | |
| 9,144,589 B2* | 9/2015 | Egana-Erazo | A61L 24/0005 |
| 9,849,150 B2* | 12/2017 | Egana-Erazo | C12N 5/0068 |
| 11,207,362 B2* | 12/2021 | Egana-Erazo | A61L 26/0042 |
| 2003/0004556 A1* | 1/2003 | McDaniel | A61K 8/494 607/88 |
| 2004/0166146 A1* | 8/2004 | Holloway | A61N 5/0616 424/449 |
| 2005/0136092 A1 | 6/2005 | Rotem et al. | |
| 2007/0239232 A1* | 10/2007 | Kurtz | G02B 6/001 607/87 |
| 2009/0105791 A1* | 4/2009 | McGinnis | A61N 5/0613 607/88 |
| 2010/0161009 A1* | 6/2010 | Forster | A61B 5/445 607/88 |
| 2010/0297193 A1 | 11/2010 | Archambeau et al. | |
| 2010/0312312 A1* | 12/2010 | Jones | A61N 5/062 607/88 |
| 2011/0144724 A1 | 6/2011 | Pryor et al. | |
| 2011/0190813 A1* | 8/2011 | Brownlee | A61L 27/50 606/214 |
| 2012/0015331 A1* | 1/2012 | Wood | A61L 27/3804 433/215 |
| 2013/0089521 A1* | 4/2013 | Eagana-Erazo | A61L 24/0005 424/93.1 |
| 2013/0102076 A1 | 4/2013 | Licamele et al. | |
| 2014/0163651 A1* | 6/2014 | Bickford | A61N 5/0616 607/90 |
| 2014/0276247 A1* | 9/2014 | Hall | A61N 1/0432 601/2 |
| 2014/0277297 A1* | 9/2014 | Harris | A61P 35/00 607/90 |
| 2016/0015761 A1* | 1/2016 | Egana-Erazo | A61L 24/0005 424/93.1 |
| 2019/0083809 A1* | 3/2019 | Zhang | A61N 5/0616 |

OTHER PUBLICATIONS

Kanimozhi et al., "Organic nanocomposite Band-Aid for chronic wound healing: a novel honey-based nanofibrous scaffold," Applied Nanoscience (2020) 10:1639-1652.*

Gelatin bandage may aid tissue repair, University of Wisconsin-Madison (http://www.wisc.edu), Jun. 13, 2002.*

Better Bandage: Microscopic Scaffolding Offers 'Simple' Solution To Treating Skin Injuries—ScienceDaily, Aug. 11, 2008.*

Lin et al., "Effects of Quantum Dots Adsorption on Algal Photosynthesis," J. Phys. Chem. C 2009, 113, 10962-10966.*

James V Moroney "Algal Photosynthesis," Encyclopedia of Life Sciences, 2001, John Willey & Sons, Ltd. www.els.net.*

Hopfner, U. et al., "Development of Photosynthetic Biomaterials for in Vitro Tissue Engineering". Acta Biomaterialia, vol. 10, pp. 2712-2717, Jan. 7, 2014.

ISR and Written Opinion for PCT/US2015048435, dated Dec. 14, 2015, 10 pages.

Extended European Search Report dated Apr. 3, 2018 for European patent application No. 15837606.1 in 7 pages.

Ippei Yamaoka et al., "Organ preservation using a photosynthetic solution", Transplantation Research, Biomed Central Ltd., London, UK, vol. 1, No. 1, Apr. 24, 2012, pp. 1-7, XP021124466, ISSN: 2047-1440, DOI: 10.1186/2047-1440-1-2.

* cited by examiner

Fig. 1: New illumination design. Light emitting dressings (A) and Cages with the new illumination system (B), are shown in this picture.

PHOTOSYNTHETIC CELLULAR SUBSTANCES AND METHODS OF USE THEREOF

BACKGROUND

1. Field of the Invention

The embodiments described herein are concerned with photosynthetic cellular substances that produce and deliver oxygen to a human or animal for use in a variety of medical, therapeutic and cosmetic applications.

2. Related Art

The use of oxygen as a therapeutic or healing agent in the medical field is well known but limited in use, primarily due to the difficulty of delivering oxygen to a human or animal. The most widely known application of oxygen is in the use of a hyperbaric chamber, which is a tightly sealed environment where the atmospheric pressure and oxygen concentration can be adjusted to higher than atmospheric levels to provide treatment for wounds and other diseases. However, the expense and difficult of use of the hyperbaric chamber make it a scarce item in health care, limiting its ability for treatment to the vast majority of patients that may benefit from it.

Additionally, the hyperbaric chamber primarily increases only the ambient oxygen that interacts with the surface of the patient's skin, and does not generally provide increased delivery of oxygen within the body. It has already been suggested that hypoxia could be partially resolved by the use of oxygen carriers. For example T. Henkel-Honke et al. (Reviewed by Henkel-Honke T., Oleg M. Artificial oxygen carriers: A current review. AANA J. 75, 205-211, 2007) mention the incorporation of oxygen carriers like hemoglobin or perfluorocarbons in scaffolds for tissue engineering. Although these carriers are able to provide oxygen immediately, they do not provide a constant source of oxygen and, thus, are useful only for a short period of time.

Moreover, in EP 1351623 implantable devices containing living cells in a chamber are disclosed for the release of substances out of the chamber. The purpose of such device is to carry and maintain functional cells, wherein the functional cells are cells that express and secrete a substance that is necessary for an organism in which the device has been implanted. The functional cells shall produce substances such as insulin or testosterone which are secreted into the organism. In order to maintain the functional cells in the device, photosynthetic cells are provided in a second chamber, separated by a semi-permeable wall that delivers oxygen to the functional cells. To maintain the photosynthetic cells that can grow only in the presence of light the cells are illuminated by a light source in the chamber. Thus, the oxygen level within the chamber can be maintained on a predetermined level.

SUMMARY

Embodiments described herein provide for systems and methods for developing and applying photosynthetic cellular substances to a human or animal for medical, therapeutic or cosmetic uses. Photosynthetic cells, such as algal cells, may be used in these substances to provide the ability to continuously generate oxygen when exposed to a light source or other oxygen-generating trigger. The substances can be developed as a standalone liquid, gel or cream, or embedded within a bandage, mesh, scaffold, surgical suture or other structure with a light source to promote oxygen production. The substances can be applied topically for medical, therapeutic or cosmetic treatments, or injected internally for generation of oxygen within one or more parts of the body.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1:
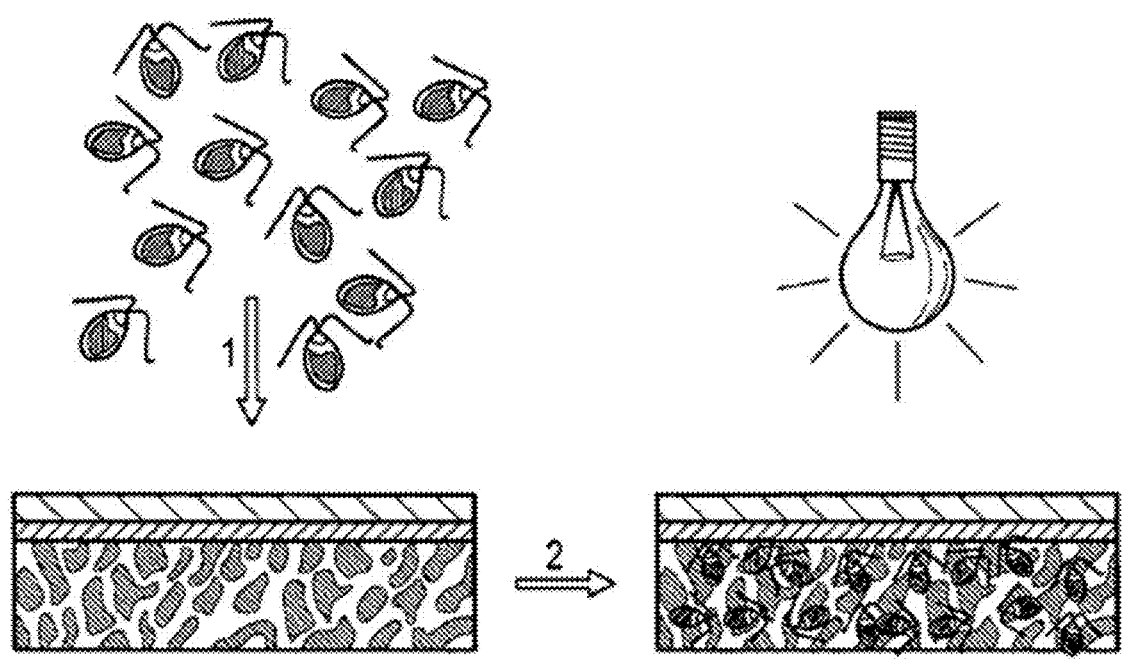
FIG. 1 illustrates how photosynthetically active cells are seeded into a structure for producing oxygen when exposed to a light source, according to an embodiment.

Certain embodiments disclosed herein provide systems and methods for developing and applying photosynthetic cellular substances to a human or animal for medical, therapeutic or cosmetic uses. Photosynthetic structures, such as algal cells, photosynthetic bacteria, isolated chloroplasts, cells obtained from vascular plants, etc. can be utilized in these substances to provide the ability to continuously generate oxygen when exposed to a light source or other oxygen-generating trigger. The substances can be developed as a standalone liquid, gel or cream, or embedded within a bandage, mesh, patch, scaffold or other structure with a light source to promote oxygen production. The substances can be applied topically for medical, therapeutic or cosmetic treatments, or injected internally for generation of oxygen within one or more parts of the body. After reading this description it will become apparent to one skilled in the art how to implement the embodiments described in various alternative embodiments and alternative applications. Thus, although various embodiments will be described herein, it is understood that these embodiments are presented by way of example only, and not limitation. As such, this detailed description of various alternative embodiments should not be construed to limit the scope or breadth of the claims.

I. Oxygen-Generating Topical Substances

In one embodiment, photosynthetic cells are photosynthetically active cells which release oxygen as a byproduct of a reaction with light. The cells can be of several different types, such as unicellular algae, but are capable of existing alongside tissues such as dermal, bone or nerve tissue, and even vascular cells that make up the vascular structure or blood and other cells transported therein.

The cells can be combined with one or more liquids, gels or even solid substances to create a topical treatment for application to one or more tissues, such as the skin, which provides the benefit of the creation of oxygen at the application site. The substances can be medicinal and designed for application to a wound or other damaged tissue to promote cellular repair and reduce the risk of infection; or therapeutic for the treatment of chronic infections or cellular damage; or cosmetic for the improvement of the health of dermal tissue. For example, a topical cream can be developed that includes algal cells and is applied to the surface of a patient's skin. The topical cream can rely upon exposure to ambient light to produce oxygen.

Algal cells provide the particular benefit of not being identified as foreign structures by the animal or human immune system, which allows them to be presented inside the human body without being attacked. In one embodiment, the algal cells can be encapsulated to minimize the risk of an allergic or other unnatural reaction by an immune system, where the encapsulation material is designed with pores to release oxygen and any other therapeutic materials that may need to be disseminated out.

In one example, the substance may be a topical wound healing ointment for applying to a cut or other damaged tissue, reducing scars, etc., where the ointment includes substances for preventing infections, reducing pain and promoting tissue regeneration. The photosynthetic substances will produce oxygen to help promote the healing of the wound.

In another example, the substance may be a chemotherapy treatment for skin cancer which is applied to a cancerous portion of the skin to provide localized therapy to affected tissue and provide the benefit of generating oxygen to promote the healing of healthy tissue.

In a further example, a photosynthetic substance can be created for use in storing organs or other living tissue structures before they are implanted into a human or animal in order to keep the organ or living tissue alive and functioning normally until it can be inserted into the human or animal and attached with the existing vascular structure. The organs or other living tissue can be placed into a solution of the photosynthetic substance, coated with the substance, wrapped in a covering or injected with the photosynthetic substance. This substance can also aid in decreasing ischemia-reperfusion injuries.

Other embodiments of the substance can be in the form of a glue or spray embedded with the photosynthetic cellular structures that can be used in different ways for more consistent application to the surface of a tissue or improving the ability of the substance to remain in contact with the tissue without wearing or washing away.

It is also important to note that the cellular structures can be designed to produce additional substances in addition to their photosynthetic properties, such as cells that produce collagen. For example, genetically-modified photosynthetic cells can be created to combine one or more additional cellular functions with photosynthetic benefits. Thus, the cellular structures can serve multiple medical, therapeutic or cosmetic purposes.

II. Oxygen-Generating Structures

Figure 4:
FIG. 4 is an image of a photosynthetic cellular substance imbedded into the structure, according to an embodiment.

The use of a photosynthetic cellular substance within a bandage, mesh, scaffold or other structure will allow the production of oxygen at the surface of the skin or exposed tissue to promote the health of the tissue or promote the healing of a wound or other exposed tissue during regeneration even if the application site is otherwise covered. Structures such as scaffolds or sutures that are embedded in deep tissue layers provide for the generation of oxygen where oxygen from the environment cannot reach. In one embodiment illustrated in FIG. 1, a mesh is embedded with algal cells and then exposed to a light source, which results in the production of oxygen by the algal cells in the mesh. FIG. 4 is an image of the algal-embedded mesh in the form of a thin, flexible material, which can easily be applied to the surface of skin or a wound or used to replace a missing tissue.

In one embodiment, a bandage or other more permanent covering can be desired to keep the substances in place, protect a wound from exposure to the ambient environment, or otherwise generally protect an exposed tissue from contact. The bandage can include an absorbent material such as a mesh or pad that can include medication, pain relieving agents or other topical substances, and this absorbent material can also be capable of containing the photosynthetic cellular structures; however, in order to provide maximum generation of oxygen, the bandage can include a light source that will ensure that the cells continue to produce oxygen if the bandage otherwise blocks ambient light.

Figure 2:
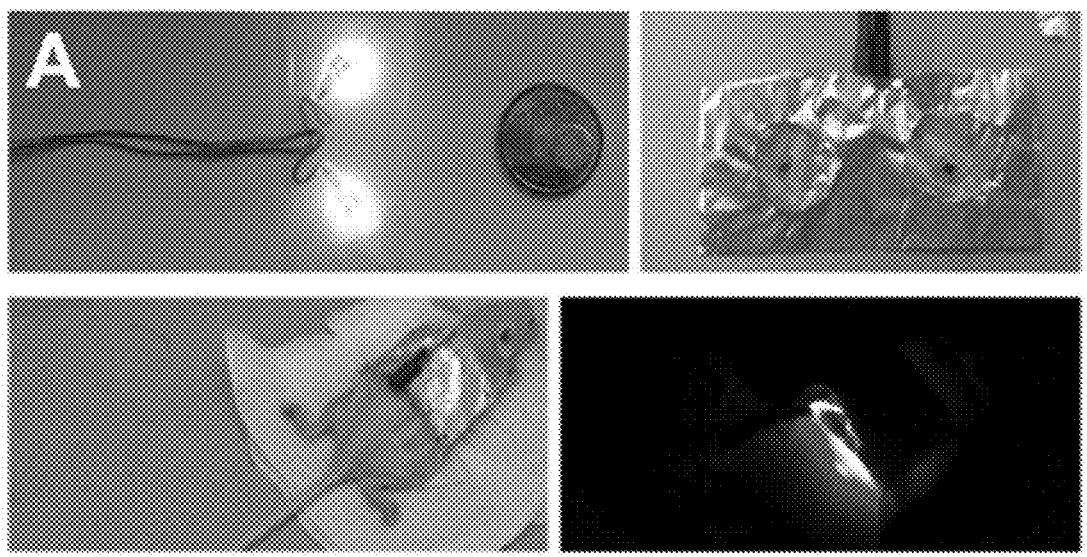
FIG. 2 is a series of images of a light-emitting dressing that incorporates the structure of FIG. 1 with a light source for application on a surface of an animal, according to an embodiment.

One embodiment of a light source embedded with a bandage is illustrated in FIG. 2. The bandage can be incorporated into a larger wearable structure such as a vest or body suit, depending on how large the surface area for application needs to be. Additionally, the bandage or other covering can be transparent or translucent to avoid the need for a separate light source to be embedded within the covering. In a separate embodiment, a wearable light producing device can be used separately from the bandage, such as for therapeutic skin treatments, facial masks, etc.

In one embodiment, the light source can be micro-LED lights that are configured to produce any number of different wavelengths, intensities and patterns of light that can be deemed to be specifically effective for certain types of treatments. The particular wavelengths of light applied can vary widely and be as general as any white light, which provides the wavelengths that cause photosynthesis and is generally considered to be in the range of approximately 380 nanometers (nm)-780 nm. However, in some embodiments, the wavelengths can be narrowly defined to stimulate a particular type of cell or produce a particular substance. For example, specific wavelengths of approximately 420 nm and approximately 660 nm can be used to stimulate Chlorophyll A, while specific wavelengths of approximately 450 nm and approximately 640 nm can be used to stimulate Chlorophyll B.

Additionally, the light can be delivered in patterns that are timed to optimize the amount of oxygen being produced by the cells. In one embodiment, light may be delivered in approximately 12 hour increments, followed by 12 hours of non-activity. The patterns can also be determined by feedback from sensors that determine the amount of oxygen being generated, as described below.

In one embodiment, the topical structure can be designed as a mask for applying to a patient's face, or in the shape of another body part such as a sock, shirt, underwear, etc. for application to that specific area of a body.

The structure can also include one or more sensors for detecting various aspects of the treatment or the condition of the tissue being treated. For example, an oxygen sensor can be embedded within a bandage to measure the amount of oxygen being produced by the photosynthetic structures in order to verify that the treatment is effective or if additional substances need to be applied. The sensors can transmit information to a computing device such as a portable electronic device or smartphone for local or remote monitoring of the patient, where an application running on the computing device or smartphone can aid in automatically monitoring the oxygen levels and determining if additional substances need to be applied. The sensors can also provide information that will allow the device to modulate the oxygen tension by, for example, regulating the intensity or pattern of light being applied over the photosynthetic structure.

Figure 3:
FIG. 3 is a series of images of an illumination container holding a photosynthetic cellular substance with at least one light source in or around the boundaries of the container to apply light for producing oxygen, according to an embodiment.

FIG. 3 illustrates a further embodiment, where a container or other structure can be devised with a light source that applies light to one or more areas of the interior area of the container from one or more different directions to maximize the application of light and the generation of oxygen within the container. A subject such as an animal can be coated with the substance or resting in a bath of a substance in order to maximize the exposure to a larger surface. As indicated above, one embodiment can comprise a container such as a cooler for storing an organ or other tissue that is being transported to a location for implanting into a patient for a medical procedure. Thus, the cooler may be fitted with one or more light sources to illuminate the interior space of the cooler, and the cooler can be filled with a liquid, gel or other substance that includes the photosynthetic cells in order to produce oxygen and help maintain the tissue or organ until it can be transplanted. Additionally, the organ or other tissue can also be perfused with photosynthetic cells to increase the supply of oxygen to the interior portion of the organ or tissue.

In another embodiment, the photosynthetic cells described herein can be used in bio-printing, for example for three-dimensional (3D) printing of tissues, organs and other biological structures and substances. Bio-printing usually requires the placement of many layers of cells into a particular structure, and these cells may not be provided with adequate oxygen due to the lack of a vascular system to feed nutrients and other important materials to the cells. Therefore, the inclusion of photosynthetic structures such as algal cells in the cellular "ink" used for bioprinting a tissue, organ or other cellular structure can provide oxygen to the other cells throughout the structure.

III. Internal Applications

The substances described above can also be configured for injection into the human or animal body for a variety of potential medical or therapeutic benefits. In one embodiment, the substances can be combined with a chemotherapy treatment to be injected into a tumor to aid in the destruction of the tumor.

In another embodiment, the substances can be injected directly into the blood stream to improve the ability of the blood to carry oxygen. Algal cells for example can supplement or replace red blood cells and deliver oxygen, for example in a diseased person or animal with a red blood cell deficiency, or for application to a specific area of the body that has tissue damage and would benefit from increased oxygen delivery. The substances can also be injected into the body during other surgical procedures to avoid risks for cardiac arrest, ischemia or hemorrhage.

In a further embodiment, photosynthetic cells can be used in conjunction with stem cell therapies in order to generate oxygen alongside injected stem cells to increase the effectiveness of the therapy or treatment. For example, if stem cells are used in a specific area of the body, the stem cell solution or substances can include the photosynthetic cells described herein, which will provide a greater source of oxygen to the stem cells and increase the effectiveness of any treatment or therapy being provided.

Figure 5:
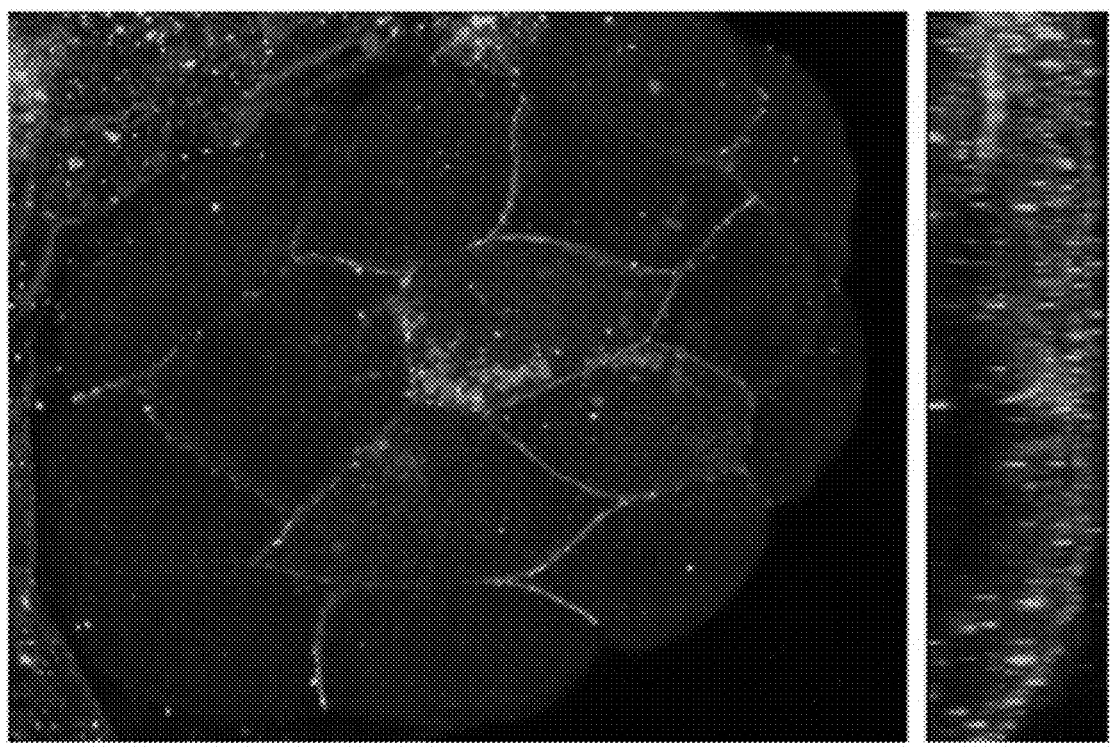
FIG. 5 is an image of the presence of photosynthetic cellular structures within a zebrafish embryo.
Figure 6:
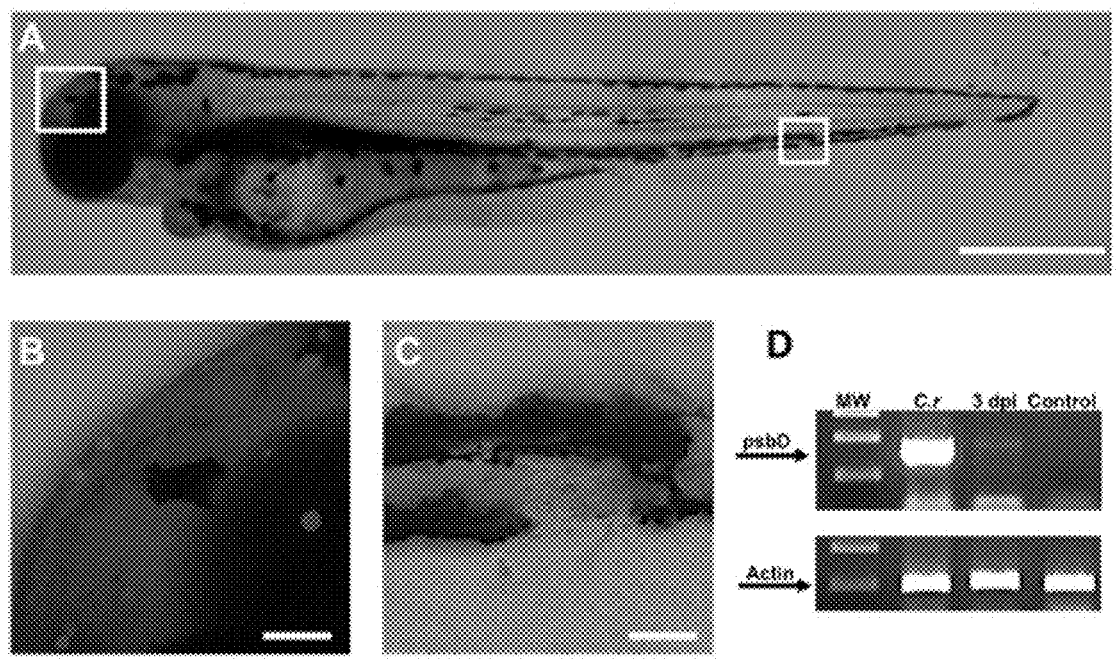
FIG. 6. is a series of images of the presence of microalgae within a zebrafish larvae.

FIG. 5 is an image of the presence of photosynthetic cellular structures within a zebrafish embryo. In this experiment, it was demonstrated that photosynthetic cellular structures can exist within a living organism. FIG. 6 is a series of images of the presence of microalgae within zebrafish larvae, again demonstrating the ability of microalgae to exist within a living organism and continuously produce oxygen.

In a further embodiment, tissue or an organ can be perfused with photosynthetic cells ex vivo for testing of drugs or other therapies. For example, a tumor can be perfused with photosynthetic cells and kept ex vivo for days to test the efficacy of an anti-cancer drug. In another example, a sample of liver tissue may be perfused with photosynthetic cells and kept ex vivo for days to test hepatotoxicity in vitro.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

IV. Applications for Radiation Therapy

Radiation therapy acts through the generation of reactive oxygen species (ROS) that are toxic for the tumor. Oxygen acts as a radiosensitizer that forms DNA-damaging free radicals and thus improves the effectiveness of a given dose of radiation. Additionally, some chemotherapeutic agents rely on oxygen for their toxic effects, such as Bleomycin, which acts through the production of reactive oxygen species (ROS).

But one significant drawback of photon radiation therapy is that tumor cells become deficient in oxygen. Some tumors can grow beyond their blood supply, causing a low-oxygen state known as hypoxia. Due to hypoxia, the pO2 in tumors is very low and big doses of radiation are required. Studies show that tumor cells in a hypoxic environment are more resistant to radiation damage than those in a normal oxygen environment. Several different methods of solving the hypoxia problem in tumors have been proposed, but none have yet effectively proposed a solution.

Therefore, in one embodiment, the photosynthetic cellular substances are applied to a tumor during radiation therapy along with light to promote photosynthesis. Oxygen is produced by the photosynthetic cells, which then increases the effectiveness of radiation in destroying the tumor. The idea here is to perfuse the tumor with photosynthetic cells and apply light and radiation therapy at the same time.

As consequence of this local and temporary increase in the oxygen tension, radiation becomes more toxic for the tumor. Moreover, with smaller doses required to obtain the same therapeutic effect, the negative side effects associated with radiation therapy will also be decreased.

The invention claimed is:
1. A system, comprising:
a device for wound care, comprising:

a bandage including an absorbent material and embedded with photosynthetic cellular structures; and a light source embedded within the bandage configured to provide a certain intensity and pattern of light to the photosynthetic cellular structures, wherein the light source is configured to produce wavelengths in the range of 380 nm to 780 nm, and wherein the photosynthetic cellular structures within the device generate oxygen when exposed to light; and a sensor configured to measure an amount of oxygen being produced by the photosynthetic cellular structures, and to transmit data associated with the amount of oxygen being produced by the photosynthetic cellular structures to a computing device.

2. The device of claim 1, wherein the light source comprises light emitting diodes (LEDs).

3. The device of claim 1, wherein the light source is configured to produce wavelengths of 420 nm.

4. The device of claim 1, wherein the light source is configured to produce wavelengths of 660 nm.

5. The device of claim 1, wherein the light source is configured to produce wavelengths of 450 nm.

6. The device of claim 1 wherein the light source is configured to produce wavelengths of 640 nm.

7. The device of claim 1, wherein the light source is configured to deliver light in a pattern where the light is alternatingly on for a first period, then off for a second period.

8. The device of claim 7, wherein the first and second periods are the same.

9. The device of claim 8, wherein the first and second periods are 12 hours.

10. The device of claim 1, wherein the photosynthetic cellular structures produce oxygen to help promote the healing of the wound.

11. The device of claim 1, wherein the absorbent material is a mesh or pad.

* * * * *